(12) United States Patent
Kamijo

(10) Patent No.: US 11,235,129 B2
(45) Date of Patent: Feb. 1, 2022

(54) TREATMENT METHOD

(71) Applicant: TERUMO KABUSHIKI KAISHA, Tokyo (JP)

(72) Inventor: Haruhiko Kamijo, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 517 days.

(21) Appl. No.: 16/176,774

(22) Filed: Oct. 31, 2018

(65) Prior Publication Data

US 2019/0126012 A1 May 2, 2019

(30) Foreign Application Priority Data

Oct. 31, 2017 (JP) .............................. JP2017-211389

(51) Int. Cl.
| | |
|---|---|
| *A61M 25/10* | (2013.01) |
| *A61M 25/00* | (2006.01) |
| *A61M 25/06* | (2006.01) |
| *A61B 17/3207* | (2006.01) |
| *A61M 25/01* | (2006.01) |

(52) U.S. Cl.
CPC ... *A61M 25/104* (2013.01); *A61B 17/320758* (2013.01); *A61M 25/005* (2013.01); *A61M 25/0026* (2013.01); *A61M 25/0662* (2013.01); *A61B 17/320725* (2013.01); *A61M 2025/0175* (2013.01); *A61M 2025/0681* (2013.01); *A61M 2025/105* (2013.01); *A61M 2210/086* (2013.01); *A61M 2210/12* (2013.01)

(58) Field of Classification Search
CPC ............ A61M 25/104; A61M 25/0026; A61M 25/0662; A61B 17/320758
See application file for complete search history.

(56) References Cited

U.S. PATENT DOCUMENTS

2014/0358123 A1* 12/2014 Ueda ................. A61M 25/0053
604/510

OTHER PUBLICATIONS

Sanghvi, Kintur, et al., "Transradial Intervention of Iliac and Superficial Femoral Artery Disease is Feasible", Journal of Interventional Cardiology, vol. 21, No. 5, 2008, pp. 385-387.

* cited by examiner

*Primary Examiner* — Nathan R Price
*Assistant Examiner* — Melissa A Snyder
(74) *Attorney, Agent, or Firm* — Buchanan Ingersoll & Rooney PC

(57) ABSTRACT

For treatment of a patient who has a lesion in each of left lower limb artery and right lower limb artery, lesions at both sides can be rather easily and completely treated. A catheter is introduced from an artery of an arm of the patient, and an atherectomy catheter is used for a lesion at one side and continuously used for a lesion at the other side without being extracted to the outside of a human body, and thus damage of an excision portion of the atherectomy catheter and an unexpected situation such as no passage through twisted blood vessels are avoided so that a burden on the patient can be reduced, the treatment can be completed within a short time, and cost reduction can be achieved by reducing the number of catheter to be used.

20 Claims, 8 Drawing Sheets

TREATMENT METHOD

CROSS-REFERENCES TO RELATED APPLICATIONS

This application claims priority to Japanese Application No. 2017-211389 filed on Oct. 31, 2017, the entire contents of which are incorporated herein by reference.

FIELD OF THE INVENTION

The present disclosure generally relates to a treatment method for performing a treatment of lower limbs by using an intervention surgery.

BACKGROUND DISCUSSION

As a treatment of a lesion in lower limb arteries, ipsilateral puncture in which a catheter is introduced from the artery of a leg that is the same as the leg having a legion, contralateral puncture in which a catheter is introduced from a leg that is opposite to the leg having a legion (cross-over method), or the like are conventionally used. However, in recent years, due to the reason such as having early release of a patient from hospital resulting from less physical burden on patient, a surgery of providing a treatment by introducing a catheter from the artery of an arm, particularly, from a radial artery (TRI: Trans Radial Intervention) is also carried out.

For example, in Journal of Interventional Cardiology Volume 21, Issue 5, October 2008, Pages 385-387, Transradial Intervention of Iliac and Superficial Femoral Artery Disease is Feasible, transdermal treatment of iliac artery and superficial femoral artery (SFA) by introducing a catheter from an arm is described.

Furthermore, in U.S. Patent Application Publication No. 2014/0358123, a double catheter assembly for treating a lesion in lower limb arteries by inserting the double catheter assembly from an arm, and a method for continuous treatment of a lesion in left and right lower limbs by selecting arbitrarily the lesion to be treated first are disclosed.

Meanwhile, there are also patients who have a lesion in each of lower left limb artery and lower right limb artery. In that case, considering a relative burden applied to a patient, it may be preferable to perform the treatment on both lesions in a single surgery.

However, the catheter used for treatment of arteries of lower limb according to introduction from an arm is disposed at a lesion only after traveling a relatively long distance inside highly twisted blood vessels and/or arteries stiffened due to progressed calcification.

In particular, among the lesions of lower limb arteries, a lesion with progressed chronic total occlusion or calcification may not be sufficiently dilated by a balloon catheter only, and thus there is a case in which an atherectomy catheter is used. Because the atherectomy catheter has a hard and long excision portion, it may be difficult to introduce the atherectomy catheter to the inside of a guiding catheter, which is disposed in a twisted blood vessel. Furthermore, a relatively long time may be required to introduce the atherectomy catheter, and, depending on each case or treatment, the path the atherectomy catheter travels may travel causing a deformation of a catheter. Furthermore, when the excision portion previously disposed inside a human body is unnecessarily extracted to the outside of a human body and disposed outside a human body, as the excision portion is broken or shaft portion is deformed due to carelessness, it may become impossible to use. As a result, when the catheter or the atherectomy catheter is replaced with another one, a relatively higher burden may be applied to a patient since the surgical time may be increased, and also the cost required for the surgery can be greater.

Thus, having a relatively short surgery time based with efficient use of the atherectomy catheter and while maintaining the functionality of the atherectomy catheter is important also from the viewpoint of medical economic efficiency such as reducing a relative burden on a patient, time associated with the use of an operating room, and a reduction in the number of catheter used.

SUMMARY

A method is disclosed for treatment of a patient who has a lesion in arteries of both left and right lower limbs, the method has a step of introducing a catheter from an artery of an arm of the patient and disposing the catheter by advancing a distal end portion of the catheter at least to the inside of an aorta of the patient, and a step of inserting an atherectomy catheter to the inside of a lumen of the disposed catheter, protruding a distal end of the atherectomy catheter from the distal end portion of the catheter, treating first a first lesion by using the atherectomy catheter, and, after treating subsequently a second lesion on the other side by changing the disposition of the atherectomy catheter, extracting the atherectomy catheter, and also inserting a catheter for treatment to the inside of the lumen of the disposed catheter, protruding a distal end of the catheter for treatment from the distal end portion of the catheter, and the second lesion is treated by the catheter for treatment.

With regard to the treatment method of the disclosure, the disposition of the catheter is changed after treating the second lesion, and then the first lesion is treated.

With regard to the treatment method of the disclosure, the disposition of the catheter is changed in a state in which the catheter for treatment is disposed inside the catheter.

With regard to the treatment method of the disclosure, the catheter for treatment is extracted from the catheter after the catheter for treatment is used for the prior treatment, and then replaced with a second catheter for treatment.

According to the disclosure, to treat a patient who has lesions in arteries of both left and right lower limbs, by inserting a catheter from an artery of an arm, treating subsequently the left and right lesions by using an atherectomy catheter, extracting the atherectomy catheter, and performing a treatment of the lesions by using a catheter for treatment, the operation can be simplified by shortening of the total travel distance of an excision portion of the atherectomy catheter, and, simultaneously, reducing the chance of breaking or damaging the excision portion of the atherectomy catheter and/or deterioration of the catheter.

In accordance with an aspect, a method is disclosed for treatment of a patient who has a lesion in arteries of both left and right lower limbs, comprising: introducing a catheter from an artery of an arm of the patient; advancing a distal end portion of the catheter at least to an aorta of the patient; inserting an atherectomy catheter inside a lumen of the catheter, protruding a distal end of the atherectomy catheter from the distal end portion of the catheter, and treating a first lesion using the atherectomy catheter in one of the left and right lower limbs; and treating a second lesion on an opposite side of the left and right lower limbs by changing a disposition of the atherectomy catheter.

Furthermore, as the atherectomy catheter is used for a lesion at one side and continuously used for a lesion at the other side without being extracted from or outside of a human body, and thus damage of the excision portion of the atherectomy catheter and an unexpected situation such as no passage through twisted blood vessels can be avoided so that a relative burden on the patient can be reduced, the treatment can be completed within a relatively short time; and costs can be reduced by reducing the number of catheters used.

DETAILED DESCRIPTION

In accordance with an exemplary embodiment, for easy understanding of the treatment method according to an embodiment, the flow of surgery is explained first. According to this treatment method, the step of introducing a catheter (for example, a guiding catheter in the present embodiment) from an artery of an arm of a patient, and disposing (or placing) the catheter by advancing a distal end portion of the catheter to at least the inside of an aorta of a patient.

Figure 1:
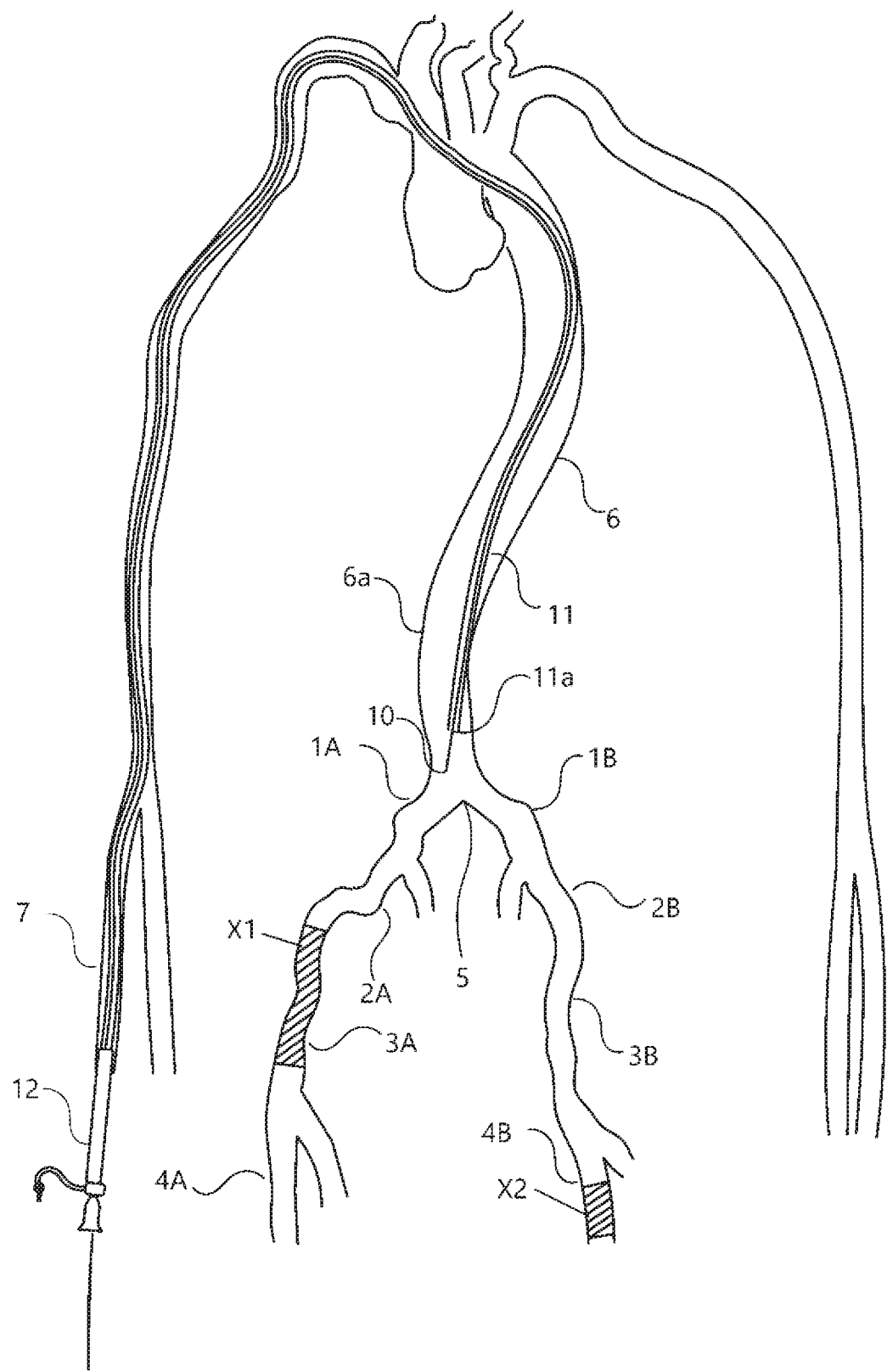
FIG. 1 is an overall explanatory diagram illustrating, with regard to a treatment method according to an embodiment, and wherein a catheter is disposed inside a blood vessel and a lesion.

FIG. 1 illustrates a state in which a lesion is present in each of left and right lower limbs and a guiding catheter 11 is disposed inside the blood vessel of a patient who has a stenosed site (lesion) X1 in a right common femoral artery 3A and a calcified stenosed site (lesion) X2 in a left superficial femoral artery 4B. In the disposition step, for example, a right radial artery 7 is punctured by a non-illustrated puncture needle, and after disposing a mini guide wire (not illustrated) inside a blood vessel, a introducer sheath 12 provided with a dilator (not illustrated) is inserted, the dilator and mini guide wire are extracted, and the guiding catheter 11 provided with a guide wire 10 is introduced via the introducer sheath 12.

In accordance with an exemplary embodiment, a hydrophilic lubricant coating for enhancing the insertion property can be applied to a surface of the guiding catheter 11 or the guide wire 10.

Next, by following the guide wire 10, the guiding catheter 11 is advanced from the artery of an arm at least to the inside of an aorta 6 of a patient. Specifically, for example, a catheter tip 11a of the guiding catheter 11 can be advanced to the vicinity of the aorta of an aortailiac bifurcation 5, and the catheter tip 11a is disposed such that the catheter tip 11a is positioned towards the entrance of a right common iliac artery 1A.

Figure 2:
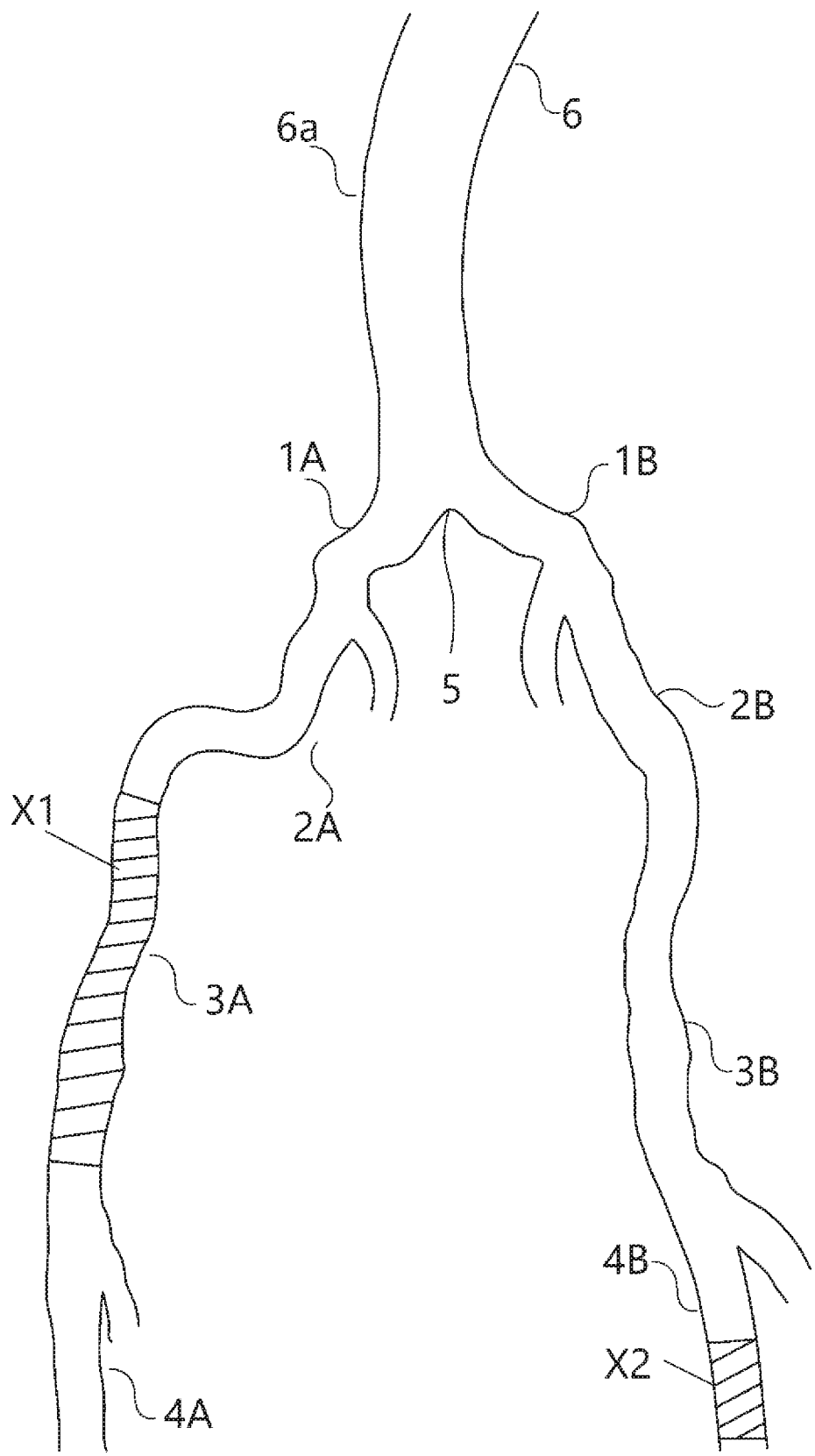
FIG. 2 is an explanatory diagram illustrating the lesion with regard to the treatment method according to the embodiment.

FIG. 2 is a diagrammatic diagram illustrating the position of the lesions (X1, X2) in lower limb arteries.

In the present embodiment, information regarding blood vessels of a patient is collected by blood vessel angiography, computed tomography (CT), or the like before the catheter treatment, and length, position, number, stenosis rate, and curvature of a lesion are evaluated based on the size, shape, or calcification level of blood vessel or presence of blood flow.

Alternatively, as a method for evaluating the symptoms of a lower limb of a patient, based on guidelines of Trans Atlantic Inter-Society II (TASC II), severity of peripheral arterial disease (PAD) according to Fontaine classification of symptoms or severity according to Rutherford classification that is based on function test such as blood pressure after an exercise tolerance test can be used. As for the evaluation of symptoms of a patient, an overall evaluation according to combination of the state of a lesion can be obtained by blood vessel angiography or image analysis by CT as described above.

In the present embodiment, the stenosed site X1, which is a chronic total occlusion (CTO), is present in the right common femoral artery 3A and the stenosed site X2, which is calcified CTO, is present in a left superficial femoral artery 4B, in which the stenosed site X1 is treated first, but the order can be an arbitrary or desired order.

Figure 3:
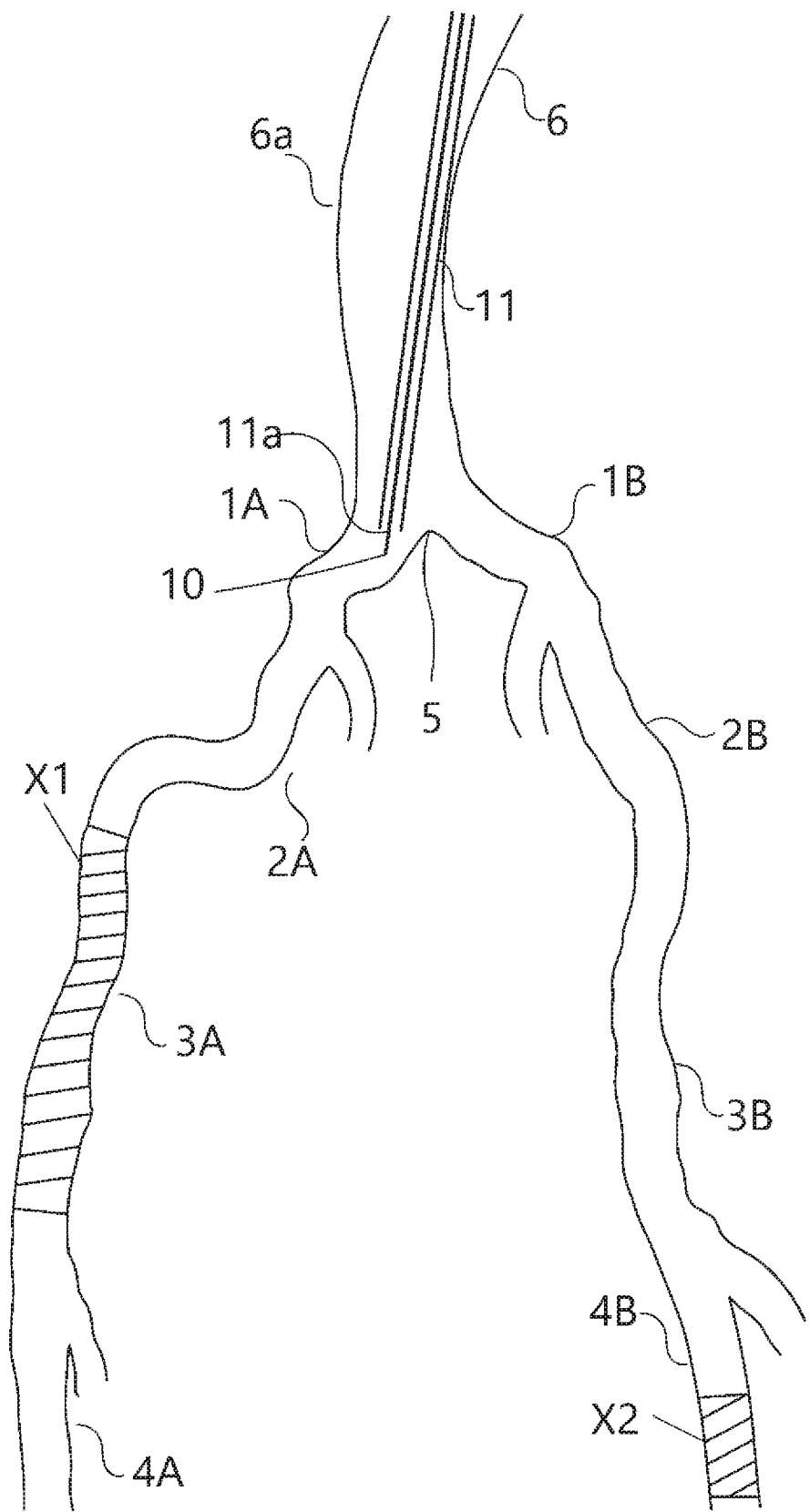
FIG. 3 is an explanatory diagram illustrating, with regard to the treatment method according to the embodiment, the selection of a blood vessel to be treated first.

FIG. 3 illustrates a state in which the guiding catheter 11 is disposed close to the vicinity of the aortailiac bifurcation 5, and, in this state, the catheter tip 11a and the distal end portion of the guide wire 10, which has been disposed inside the guiding catheter 11 and introduced with the guiding catheter 11 are positioned towards the stenosed site X1 that is selected to be treated first.

Specifically, the left side of an abdominal aorta 6a, which is at the opposite side of the right common iliac artery 1A of the aortailiac bifurcation 5, is contacted with the guiding catheter 11, and the opening portion of the catheter tip 11a is positioned towards the right common iliac artery 1A.

Figure 4:
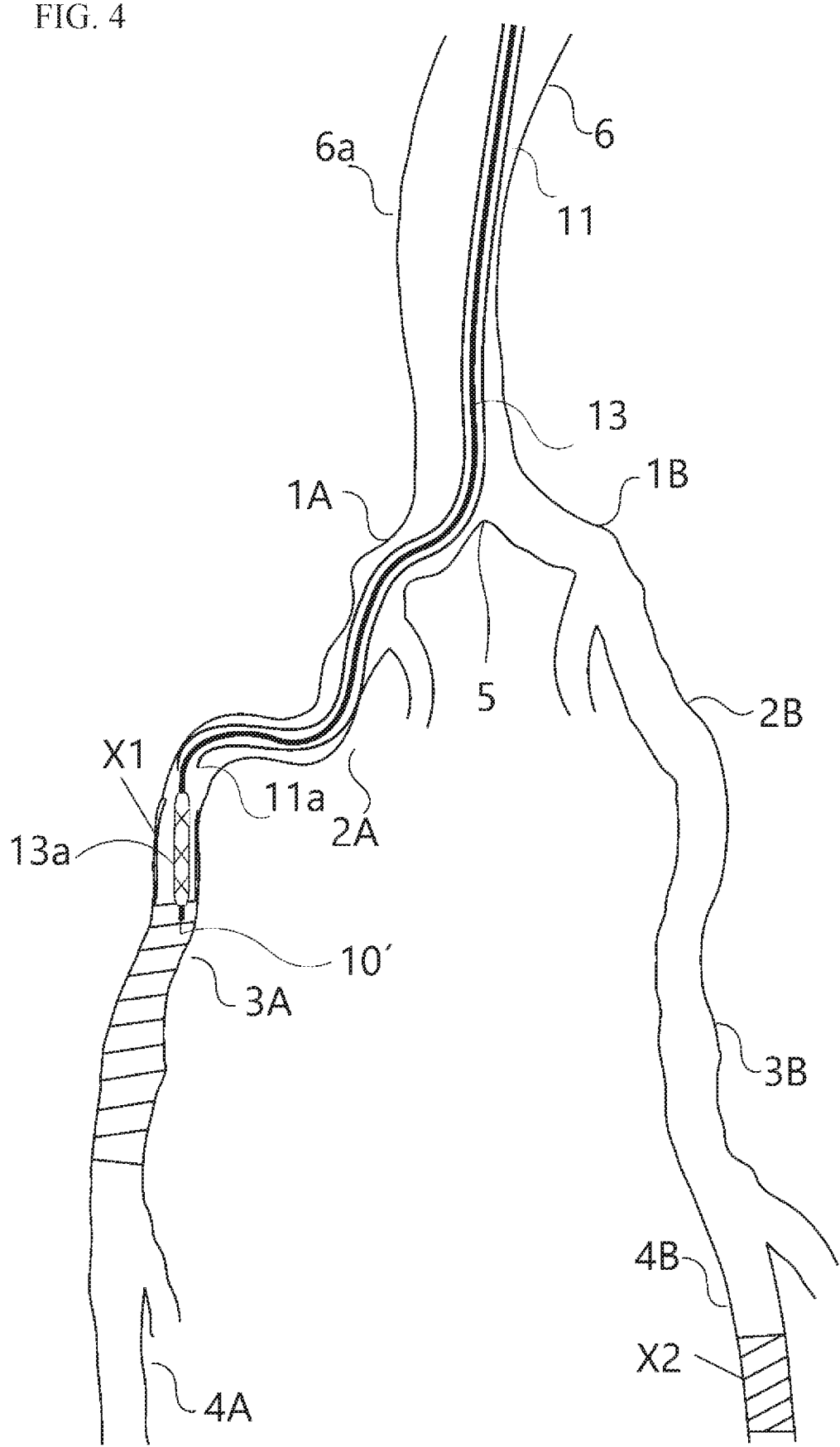
FIG. 4 is an explanatory diagram illustrating, with regard to the treatment method according to the embodiment, a state in which a guiding catheter is delivered to the front of a first lesion and the excision portion of an atherectomy catheter is disposed at the first lesion for treatment.

FIG. 4 illustrates a state in which an atherectomy catheter 13 is maintained at the stenosed site X1 and the treatment is carried out (or performed). The atherectomy catheter 13 has an excision portion 13a at the distal end portion, and, according to rotation of the atherectomy catheter 13, a passage (hole) for passing a catheter for treatment or a guide wire, which will be described later, through the chronic total occlusion (CTO) is formed, or the passage can be dilated.

In FIG. 4, to treat the stenosed site X1 as a lesion in the right common femoral artery 3A, the guide wire 10 is disposed in front of (proximally of) the right common femoral artery 3A. Subsequently, the guiding catheter 11 is advanced along the guide wire 10, and the catheter tip 11a is disposed up to the front (proximal side) of the lesion, specifically, for example, proximal (i.e., in front) of the right common femoral artery 3A. Herein, in accordance with an exemplary embodiment, the guide wire 10 can be replaced with a guide wire 10' having a small outer diameter than guide wire 10. In accordance with an exemplary embodiment, the guide wire 10' is left as much as possible in a state in which the guide wire 10' is inserted into the stenosed site X1, and, from the opening portion of the disposed catheter tip 11a, the rotational atherectomy catheter 13 is advanced to the stenosed site X1 side along a guide wire 10' and delivered to the stenosed site X1 so that an excision portion 13a is disposed at the stenosed site X1.

Subsequently, by rotating the excision portion 13a, emboli can be excised and a hole can be created in the stenosed site X1.

Once a hole is created in the stenosed site X1, the atherectomy catheter 13 and the guide wire 10' are retreated (i.e., removed) and the excision portion 13a is kept (or maintained) inside the lumen of the guiding catheter 11.

In accordance with an exemplary embodiment, the atherectomy catheter has an excision portion and is capable of dilating a lesion by excising, penetrating, or incising a lesion of occluded or constricted blood vessel. Examples of a method for excision include grinding, cutting, cutting off, penetration, incision, laser irradiation, cleaning, or dissolving emboli, and specifically indicate a rotation type, a cutting balloon, a scoring balloon, a penetration catheter, an incision catheter, or a laser ablation catheter.

Figure 5:
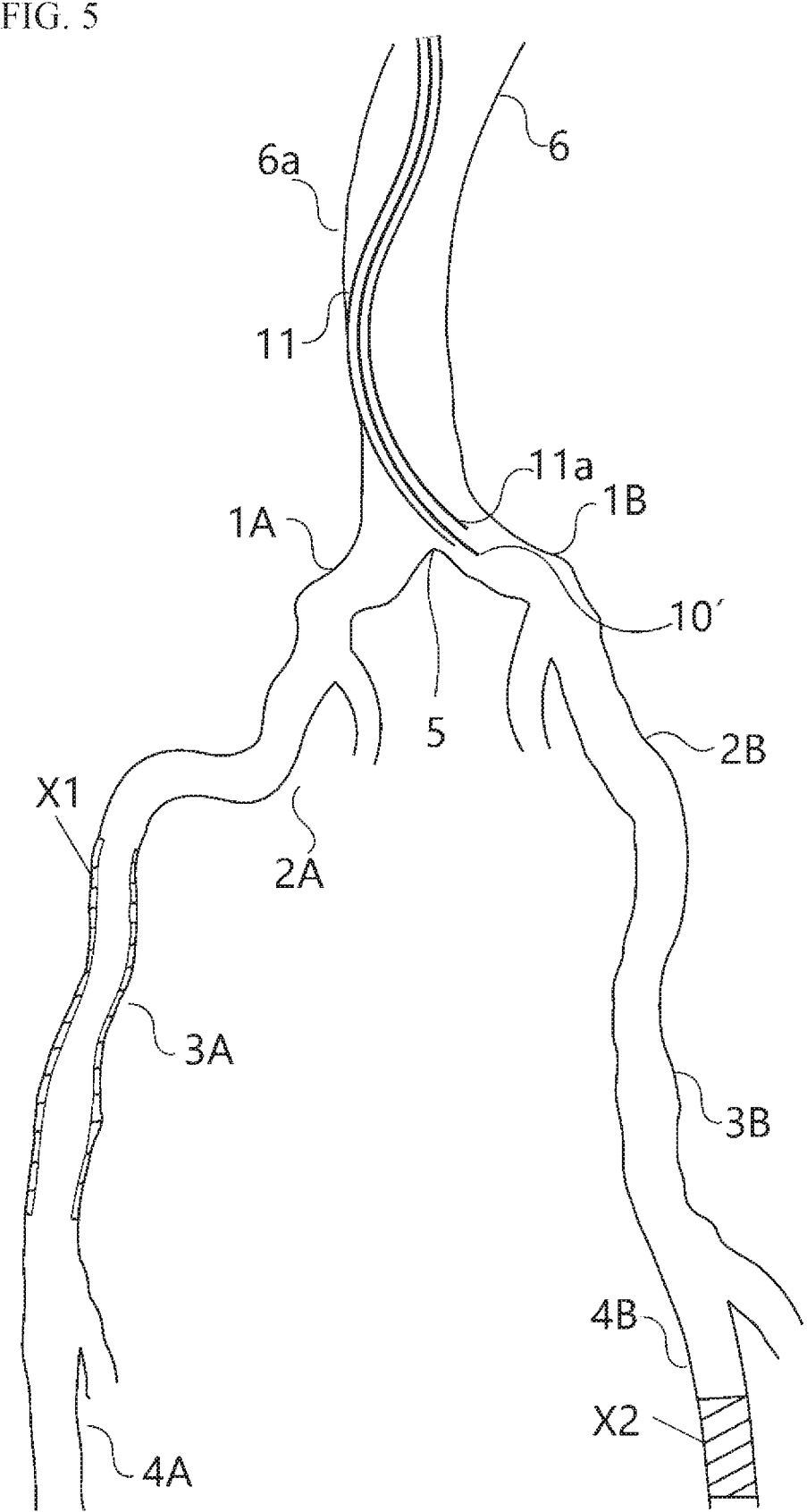
FIG. 5 is an explanatory diagram illustrating, with regard to the treatment method according to the embodiment, a state in which, after completing the treatment of a lesion in blood vessel at one side, the catheter is retreated to a bifurcated portion, and a distal end portion of the catheter is positioned towards a common iliac artery an the opposite side.

Subsequently, treatment of the stenosed site X2 (lesion) at the other side is carried out (or performed). FIG. 5 is a diagram illustrating a state in which, after treating first the stenosed site X1 of the right common femoral artery 3A, the catheter tip 11a is positioned towards a left common iliac artery 1B side to treat the stenosed site X2 of a left superficial femoral artery 4B.

Subsequently, the guide wire 10' is inserted to the left common iliac artery 1B and disposed over the stenosed site X2 of the left superficial femoral artery 4B.

Next, along the guide wire 10', the guiding catheter 11 is advanced from the left common iliac artery 1B via the left external iliac artery 2B and the left femoral artery 3B such that the guiding catheter 11 is not accidently introduced into another bifurcated portion, and disposed in the left superficial femoral artery 4B.

Figure 6:
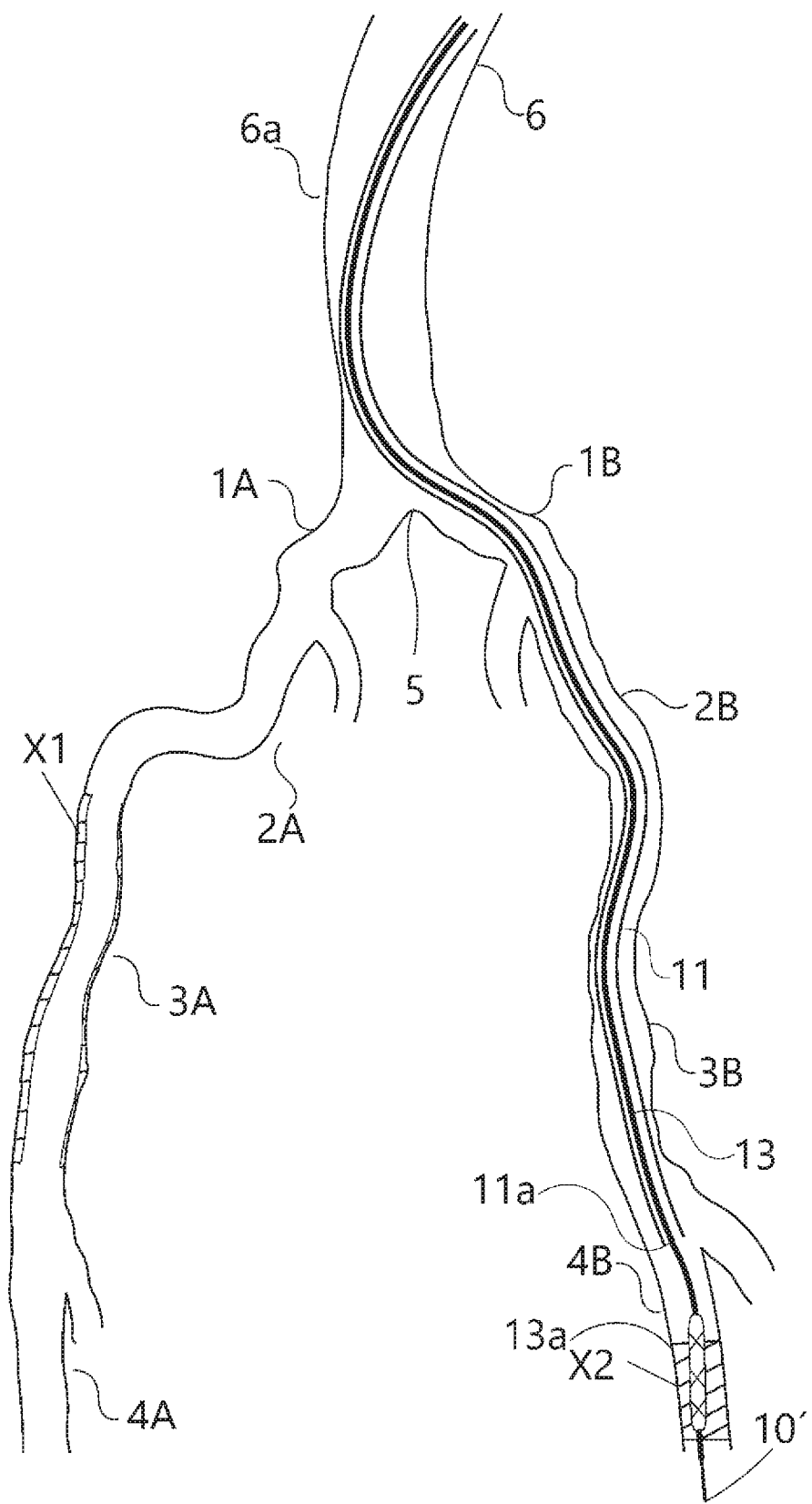
FIG. 6 is an explanatory diagram illustrating, with regard to the treatment method according to the embodiment, a state in which the guiding catheter is delivered to the front (or proximal side) of a second lesion and the excision portion of the atherectomy catheter is disposed at the second lesion for treating the second lesion.

Subsequently, as illustrated in FIG. 6, the atherectomy catheter 13 having been used for treatment of the first lesion is advanced inside the disposed guiding catheter 11, the excision portion 13a is protruded from the opening portion of the catheter tip 11a, and the excision portion 13a is disposed at the stenosed site X2. Subsequently, the excision portion 13a is rotated to create a hole in the stenosed site X2.

After the treatment, the guiding catheter 11 is advanced into the stenosed site X2, and the catheter tip 11a is disposed over the stenosed site X2 (i.e., the catheter tip 11a is placed distally of a distal end of the stenosed site X2). The atherectomy catheter 13 and the guide wire 10' after use are retreated to the hand-side (proximal side), and the atherectomy catheter 13 is extracted (or removed) to the outside of a human body. In accordance with an exemplary embodiment, there was no deformation or deterioration of an excision portion of the atherectomy catheter, and the shaft portion showed no deformation.

Figure 7:
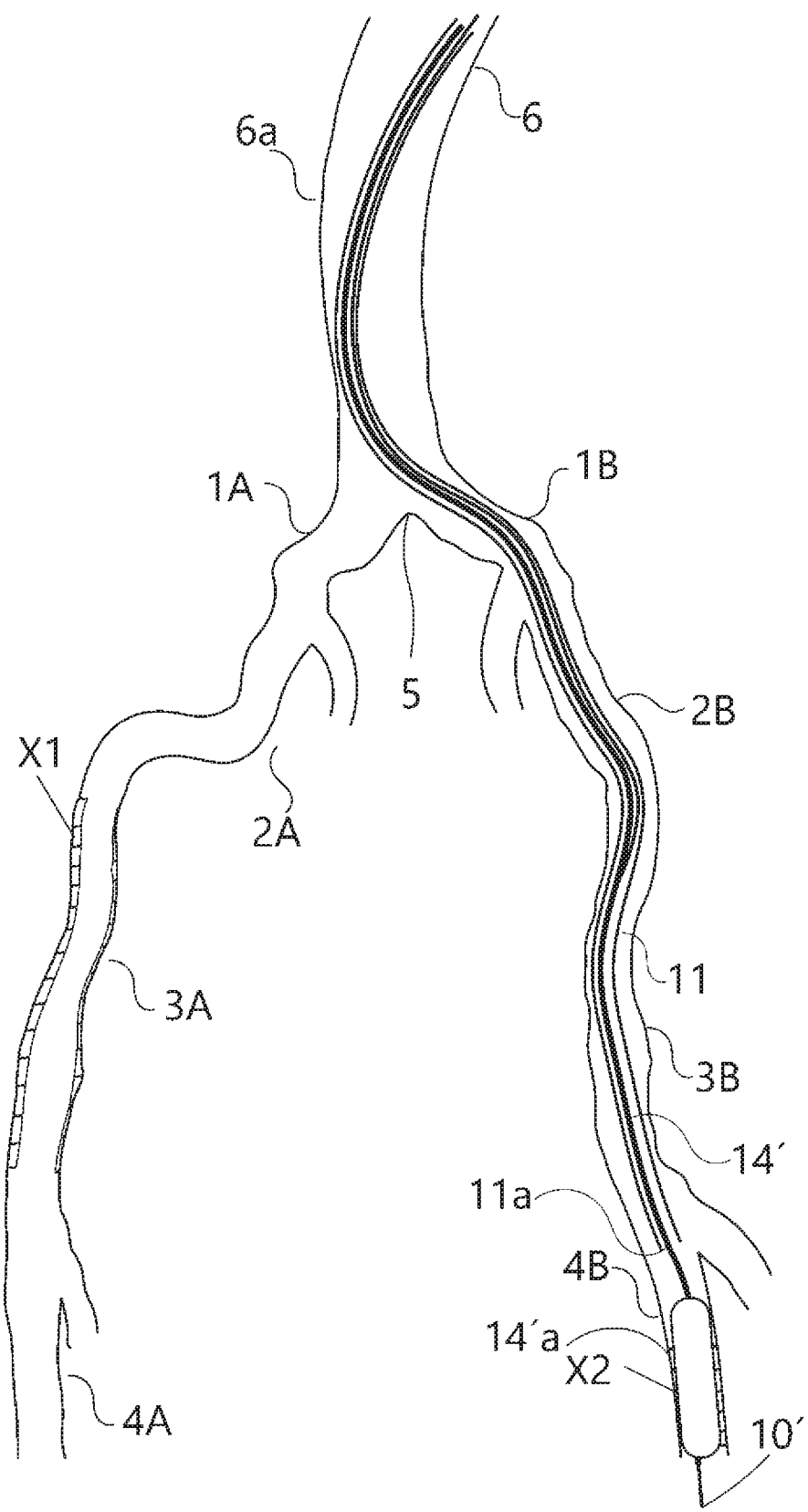
FIG. 7 is an explanatory diagram illustrating, with regard to the treatment method according to the embodiment, a state in which excision of the second lesion is completed, a drug coated balloon is disposed and dilated, and application of the pharmaceutical is completed.

Next, a drug coated balloon 14' can be inserted into the guiding catheter 11 and disposed at (i.e., placed in) the stenosed site X2. As illustrated in FIG. 7, the guiding catheter 11 is retreated to the hand-side (proximal side), and a drug coated balloon 14'a is exposed (expanded) inside the stenosed site X2. The drug coated balloon 14'a is dilated, and application of the pharmaceutical can be carried out (performed) together with dilating of a lesion, and, according to shrinkage of the drug coated balloon 14'a followed by extraction to the outside of a human body, treatment of the stenosed site X2 is completed. Herein, advancing the guiding catheter 11 to the stenosed site X2 can be carried out (or performed) for preventing, during the passage of the drug coated balloon 14'a through the stenosed site X2, the loss of drug from the balloon surface due to friction.

Subsequently, the guide wire 10' and the guiding catheter 11 are retreated to the hand-side (proximal side). If necessary, treatment of the stenosed site X1 can be carried out (performed) after changing the disposition (i.e., position). Specifically, for example, the guide wire 10' can be advanced and disposed over the stenosed site X1, the guide wire 10' the guiding catheter 11 is introduced to the stenosed site X2, and the catheter tip 11a is disposed over the stenosed site X2 (i.e., the catheter tip 11a is placed distally of a distal end of the stenosed site X2).

Figure 8:
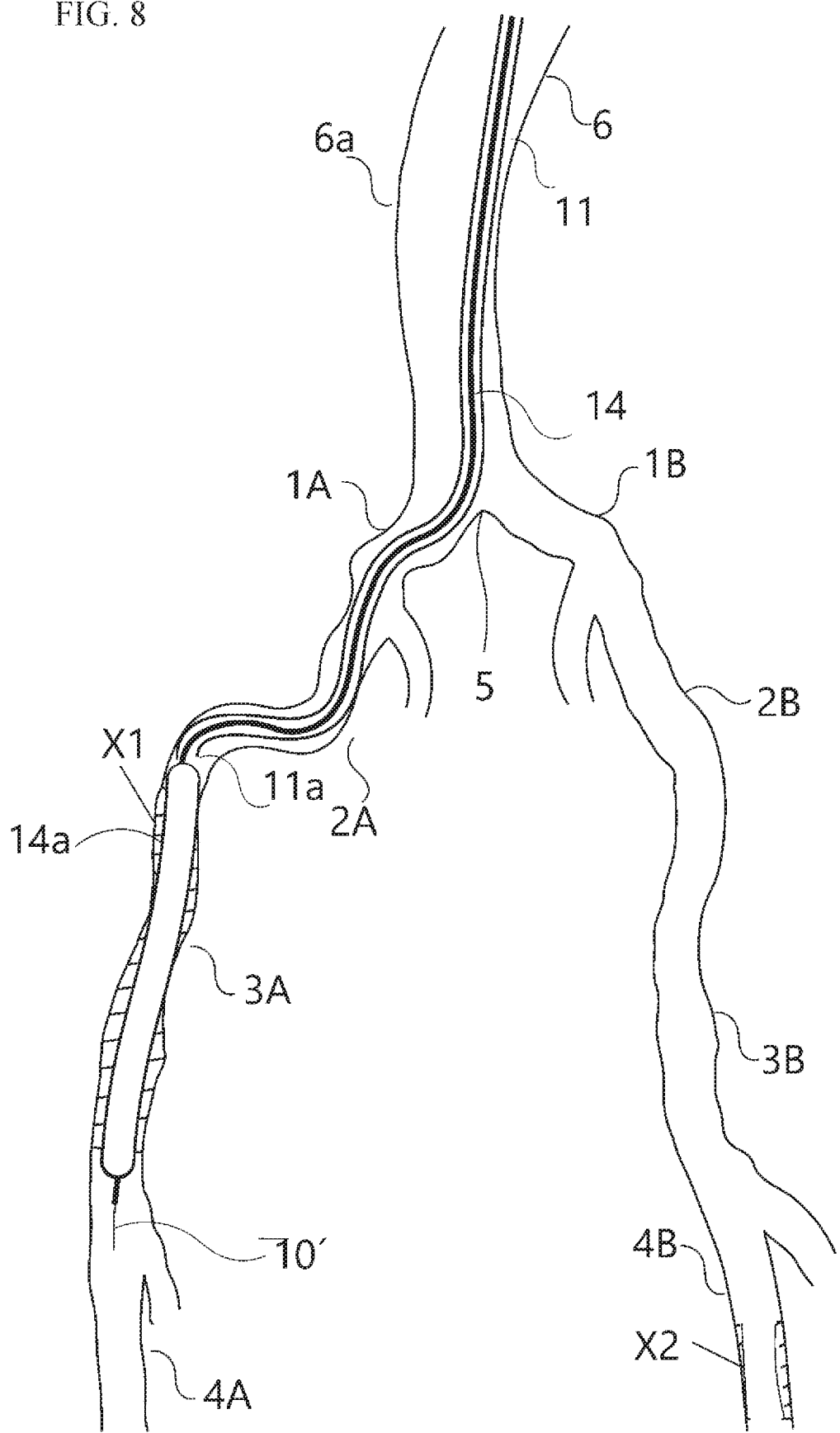
FIG. 8 is an explanatory diagram illustrating, with regard to the treatment method according to the embodiment, a state in which, after completing the treatment of the second lesion, a drug coated balloon treats the first lesion.

Next, as illustrated in FIG. 8, a drug coated balloon 14 is inserted to the guiding catheter 11, and then disposed (i.e., placed) at the stenosed site X1. The guiding catheter 11 is retreated to the hand-side, and a drug coated balloon 14a is exposed (expanded) inside the stenosed site X1. The drug coated balloon 14a is dilated and application of the drug is carried out (performed) together with dilating of a lesion, and, according to shrinkage of the drug coated balloon 14a followed by extraction to the outside of a human body, treatment of the stenosed site X1 is completed.

After that, when a treatment using the guiding catheter 11 is not performed, the guiding catheter 11 can be extracted directly with other devices from the blood vessel, and the treatment can be completed.

As described above, by the treatment method based on the steps shown in the embodiments, highly efficient treatment of a lesion in arteries of lower limbs having lesions both in left and right sides can be achieved while lowering or reducing a relative burden on a patient, and, at the same time, costs can be reduced by reducing the number of catheters used.

Subsequently, the disclosure is explained in detail based on appropriate examples, the disclosure is not limited to the content of the examples.

Examples

In accordance with an exemplary embodiment, the intervention devices used for the treatment method are an introducer sheath 12 which has outer diameter of 2.8 mm, a distal end inner diameter of 2.4 mm, and a total length of 130 mm and is provided with a dilator and a hemostasis valve; a guiding catheter 11 which has outer diameter of 2.4 mm, an inner diameter of 2.2 mm, and a total length of 1550 mm; and an atherectomy catheter for treating the stenosed site X1 of which lesion has length of 100 mm and the stenosed site X2 with progressed calcification of which lesion has a length of 20 mm. The intervention devices also include a rotational atherectomy catheter 13 which has a total length of 2000 mm and an excision portion with an outer diameter of 2.1 mm and a length of 10 mm, a catheter for treatment, a guide wire 10 with an outer diameter of 0.9 mm (total length of 3800 mm), and a guide wire 10' with outer diameter of 0.4 mm (total length of 4500 mm). Furthermore, a balloon drug coated balloon catheter 14 can be used which has a dilated balloon diameter of 7 mm and a balloon length of 100 mm for treating the stenosed site X1 and a balloon drug coated balloon catheter 14' which has a dilated balloon diameter of 5 mm and a balloon length of 20 mm for treating the stenosed site X2.

By using those intervention devices, a treatment simulation was carried out (or performed) for a blood vessel model as described below.

For a patient who has the stenosed site X1 in the right common femoral artery 3A and the stenosed site X2 in the left superficial femoral artery 4B, puncturing was performed for the right radial artery 7. After disposing the guide wire 10 inside a blood vessel, the introducer sheath 12 was inserted. Then, after extracting the dilator, the guiding catheter 11 was introduced via the introducer sheath 12.

Next, the guiding catheter 11 was advanced, from the right radial artery 7, up to the abdominal aorta 6a of the patient and the catheter tip 11a was advanced, along the guide wire 10, to the vicinity of the aorta 6 of the aortailiac bifurcation 5.

In accordance with an exemplary embodiment, to treat first the stenosed site X1 of the right common femoral artery 3A, the catheter tip 11a is disposed at the entrance of the right common femoral artery 3A. At that time, the guiding catheter 11 was in contact with the left side of the abdominal aorta 6a.

Replacement with the guide wire 10' which has a smaller outer diameter than the guide wire 10 was made, and, while supporting the guide wire 10' with the guiding catheter 11, the atherectomy catheter 13 was protruded, along the guide wire 10', to the stenosed site X1 side, and, by delivering the atherectomy 13 to the stenosed site X1, the excision portion 13a was disposed at the stenosed site X1.

Subsequently, the excision portion 13a was rotated, and, under slight advancement of the excision portion, emboli in the stenosed site X1 were excised and widening of the stenosed site X1 was carried out by passing through the stenosed site X1. The atherectomy catheter 13 was retreated from the stenosed site X1 to the hand-side (proximal side) by operating the hand portion. Subsequently, the guiding catheter 11 and the guide wire 10' were also similarly retreated to the hand-side. The atherectomy catheter 13 was not extracted and the excision portion 13a was disposed inside the guiding catheter.

Next, by rotating the hand hub of the guiding catheter 11, the catheter tip 11a was positioned towards the left common iliac artery 1B. The guide wire 10' was inserted to the entrance of the left common iliac artery 1B, and disposed over the stenosed site of the left superficial femoral artery 4B.

Subsequently, along the guide wire 10', the catheter tip 11a was disposed in front (proximally) of the stenosed site X2 of the left superficial femoral artery 4B.

Subsequently, the atherectomy catheter 13 was advanced inside the guiding catheter 11 which has been disposed along the guide wire 10', the atherectomy catheter 13 was protruded from the catheter tip 11a, the excision portion 13a was disposed at the stenosed site X2, the excision portion 13a was rotated, and plaque at the stenosed site was excised to dilate the X2.

After the treatment, while the guide wire 10' and the guiding catheter 11 are left in a disposed state, the atherectomy catheter 13 was retreated to the hand-side, and additionally extracted to the outside (or removed from) of a human body. At that time, as there was no deterioration such as breakage or deformation found in the atherectomy catheter 13, or a problem in terms of the extraction.

Next, the guiding catheter 11 was advanced to the stenosed site X2, and the catheter tip 11a was disposed over the stenosed site X2. The drug coated balloon 14' was advanced to the inside of the disposed guiding catheter 11, and the drug coated balloon portion 14'a was disposed at the stenosed site X2. The guiding catheter 11 was retreated and the drug coated balloon portion 14'a was exposed to the stenosed site. After the exposure, the drug coated balloon portion 14'a was dilated, application of a pharmaceutical was carried out for the lesion, and the drug coated balloon portion 14'a was shrunken, retreated to the hand-side, and then the coated balloon portion 14'a was extracted (or removed from), for example, a human body.

Furthermore, the guiding catheter 11 and the guide wire 10' were retreated to the hand-side, and the catheter tip 11a was disposed in the vicinity of the aortailiac bifurcation 5.

Next, by rotating the hand hub of the guiding catheter 11, the catheter tip 11a was positioned towards the right common femoral artery 3A. The guide wire 10' was inserted to the entrance of the right common iliac artery 1A, and disposed over the stenosed site X1 of the right common femoral artery 3A.

Subsequently, along the guide wire 10', the catheter tip 11a was disposed over the stenosed site X1 of the right common femoral artery 3A.

The drug coated balloon 14 was advanced to the inside of the disposed guiding catheter 11, and the drug coated balloon portion 14a was disposed at the stenosed site X1. The guiding catheter 11 was retreated and the drug coated balloon portion 14a was exposed to the stenosed site. After the exposure, the drug coated balloon portion 14a was dilated, application of a pharmaceutical was carried out for the lesion, and the drug coated balloon portion 14a was shrunken, retreated to the hand-side, and then the drug coated balloon portion 14a as was extracted (or removed) from, for example, a human body.

Furthermore, the guiding catheter 11 and the guide wire 10' were retreated to the hand-side, and additionally extracted (or removed) from, for example a human body to complete the treatment.

For a patient who has a lesion in arteries of both left and right lower limbs, an atherectomy catheter can be used for a lesion at one side and continuously used for a lesion at the other side (or opposite) without being extracted to the outside, for example, of a human body, and thus damage of an excision portion of the atherectomy catheter and an unexpected situation such as no passage through twisted blood vessels can be avoided so that a burden on the patient can be reduced, the treatment can be completed within a relatively short time, and costs can be reduced by reducing the number of catheter to be used.

The detailed description above describes to a treatment method for performing a treatment of lower limbs by using an intervention surgery. The disclosure is not limited, however, to the precise embodiments and variations described. Various changes, modifications and equivalents can be effected by one skilled in the art without departing from the spirit and scope of the disclosure as defined in the accompanying claims. It is expressly intended that all such changes, modifications and equivalents which fall within the scope of the claims are embraced by the claims.

What is claimed is:

1. A treatment method of a patient who has a lesion in arteries of both left and right lower limbs, comprising:
   introducing a catheter from an artery of an arm of the patient;

disposing the catheter by advancing a distal end portion of the catheter at least to an aorta of the patient;

inserting an atherectomy catheter inside a lumen of the disposed catheter, protruding a distal end of the atherectomy catheter from the distal end portion of the catheter, treating first a first lesion using the atherectomy catheter in one of the left and right lower limbs;

after treating the first lesion subsequently changing the disposition of the atherectomy catheter without being extracted from the patient to a second lesion on an opposite side of the left and right lower limbs;

treating the second lesion with the atherectomy catheter;

extracting the atherectomy catheter; and inserting a first treatment catheter inside the lumen of the disposed catheter, protruding a distal end of the first treatment catheter from the distal end portion of the catheter, and treating the second lesion.

2. The treatment method according to claim 1, comprising:

changing the disposition of the catheter after the treating of the second lesion with the first treatment catheter, and then treating the first lesion with a treatment catheter.

3. The treatment method according to claim 2, wherein the treatment catheter is the first treatment catheter, the method comprising:

treating the first lesion with the first treatment catheter.

4. The treatment method according to claim 1, comprising:

changing the disposition of the catheter in a state in which the atherectomy catheter is disposed inside the catheter.

5. The treatment method according to claim 1, comprising:

extracting the first treatment catheter from the catheter after the first treatment catheter treats the second lesion; and replacing the first treatment catheter with a second treatment catheter.

6. The treatment method according to claim 1, wherein the first treatment catheter is a drug coated balloon catheter.

7. The treatment method according to claim 3, further comprising:

dilating the first treatment catheter in the first lesion and/or the second lesion.

8. The treatment method according to claim 1, wherein the lesion in the arteries of both the left and right lower limbs are each stenosed sites.

9. The treatment method according to claim 1, wherein the artery of the arm of the patient is a radial artery.

10. The treatment method according to claim 1, comprising:

advancing the distal end portion of the catheter to the aorta of the patient over a guide wire.

11. The treatment method according to claim 1, wherein the catheter and the atherectomy catheter are not withdrawn from the patient until after the treatment of the first lesion and the second lesion.

12. A treatment method of a patient who has a lesion in arteries of both left and right lower limbs, comprising:

introducing a catheter from an artery of an arm of the patient;

advancing a distal end portion of the catheter at least to an aorta of the patient;

inserting an atherectomy catheter inside a lumen of the catheter, protruding a distal end of the atherectomy catheter from the distal end portion of the catheter, and treating a first lesion using the atherectomy catheter in one of the left and right lower limbs;

changing the disposition of the atherectomy catheter to a second lesion on an opposite side of the left and right lower limbs without extracting the atherectomy catheter from the patient; and treating the second lesion with the atherectomy catheter.

13. The treatment method according to claim 12, further comprising:

extracting the atherectomy catheter; and inserting a first drug coated balloon catheter inside the lumen of the disposed catheter, protruding a distal end of the first drug coated balloon catheter from the distal end portion of the catheter, and treating the second lesion with the first drug coated balloon catheter.

14. The treatment method according to claim 12, comprising:

changing the disposition of the catheter after the treating of the second lesion with the first treatment catheter, and then treating the first lesion with a treatment catheter.

15. The treatment method according to claim 12, comprising:

changing the disposition of the catheter in a state in which the atherectomy catheter is disposed inside the catheter.

16. The treatment method according to claim 13, comprising:

extracting the first drug coated balloon catheter from the catheter after the first drug coated balloon catheter is used; and replacing the first drug coated balloon catheter with a second drug coated balloon catheter for treatment of the first lesion.

17. The treatment method according to claim 13, wherein the first lesion and the second lesion are stenosed sites, the method further comprising:

dilating the first drug coated catheter in the first lesion and/or the second lesion.

18. The treatment method according to claim 12, wherein in the lesion in the arteries of both the left and right lower limbs are each stenosed sites, and the artery of the arm of the patient is a radial artery.

19. The treatment method according to claim 12, comprising:

advancing the distal end portion of the catheter to the aorta of the patient over a guide wire.

20. A treatment method for treatment of a patient who has a lesion in arteries of both left and right lower limbs, comprising:

introducing a catheter from an artery of an arm of the patient;

disposing the catheter by advancing a distal end portion of the catheter at least to an aorta of the patient;

inserting an atherectomy catheter inside a lumen of the disposed catheter, protruding a distal end of the atherectomy catheter from the distal end portion of the catheter, treating first a first lesion using the atherectomy catheter in one of the left and right lower limbs;

after treating the first lesion changing the disposition of the atherectomy catheter to a second lesion on an opposite side of the left and right lower limbs;

treating the second lesion with the atherectomy catheter;

extracting the atherectomy catheter;

inserting a first treatment catheter inside the lumen of the disposed catheter, protruding a distal end of the first treatment catheter from the distal end portion of the catheter, and treating the second lesion; and changing the disposition of the catheter after the treating of the second lesion with the first treatment catheter, and then treating the first lesion with a treatment catheter.

\* \* \* \* \*